United States Patent [19]

Gmeinder

[11] Patent Number: 4,830,613
[45] Date of Patent: May 16, 1989

[54] FOOT-OPERATED STARTER FOR A DENTAL TREATMENT LOCATION

[75] Inventor: Hermann Gmeinder, Warthausen-Oberhofen, Fed. Rep. of Germany

[73] Assignee: Kaltenbach & Voigt GmbH & Co., Fed. Rep. of Germany

[21] Appl. No.: 27,863

[22] Filed: Mar. 19, 1987

[30] Foreign Application Priority Data

Apr. 4, 1986 [DE] Fed. Rep. of Germany ....... 3611407

[51] Int. Cl.$^4$ .............................................. A61C 1/02
[52] U.S. Cl. ......................................... 433/28; 433/98
[58] Field of Search ....................... 433/28, 27, 98, 101

[56] References Cited

U.S. PATENT DOCUMENTS 4,106,198  8/1978  Childress ............................... 433/28
4,430,062  2/1984  Henrichsen et al. ................... 433/28
4,479,182  10/1984  Beier ..................................... 433/28

Primary Examiner—Gene Mancene
Assistant Examiner—Adriene J. Lepiane
Attorney, Agent, or Firm—Scully, Scott, Murphy & Presser

[57] ABSTRACT

A foot-operated starter or controller for a dental treatment apparatus possessing a patient's or dental chair and a plurality of treating instruments which are arranged in separate repositories, including actuating elements through the actuation of which there can be initiated or varied different functions of the applicable treatment location. The actuating elements are interconnected with a switching or junction circuit arrangement, which is connected in such a manner with display devices indicative of the removal of the treating instruments from their repositories, such that merely upon withdrawal of at least one treating instrument from its repository, the actuating elements serve for the regulation of the adjusted setting of the applicable treating instrument, whereas at the presence of the collective treating instruments in their repositories they serve for the setting of the adjusted positions of the dental chair.

2 Claims, 1 Drawing Sheet

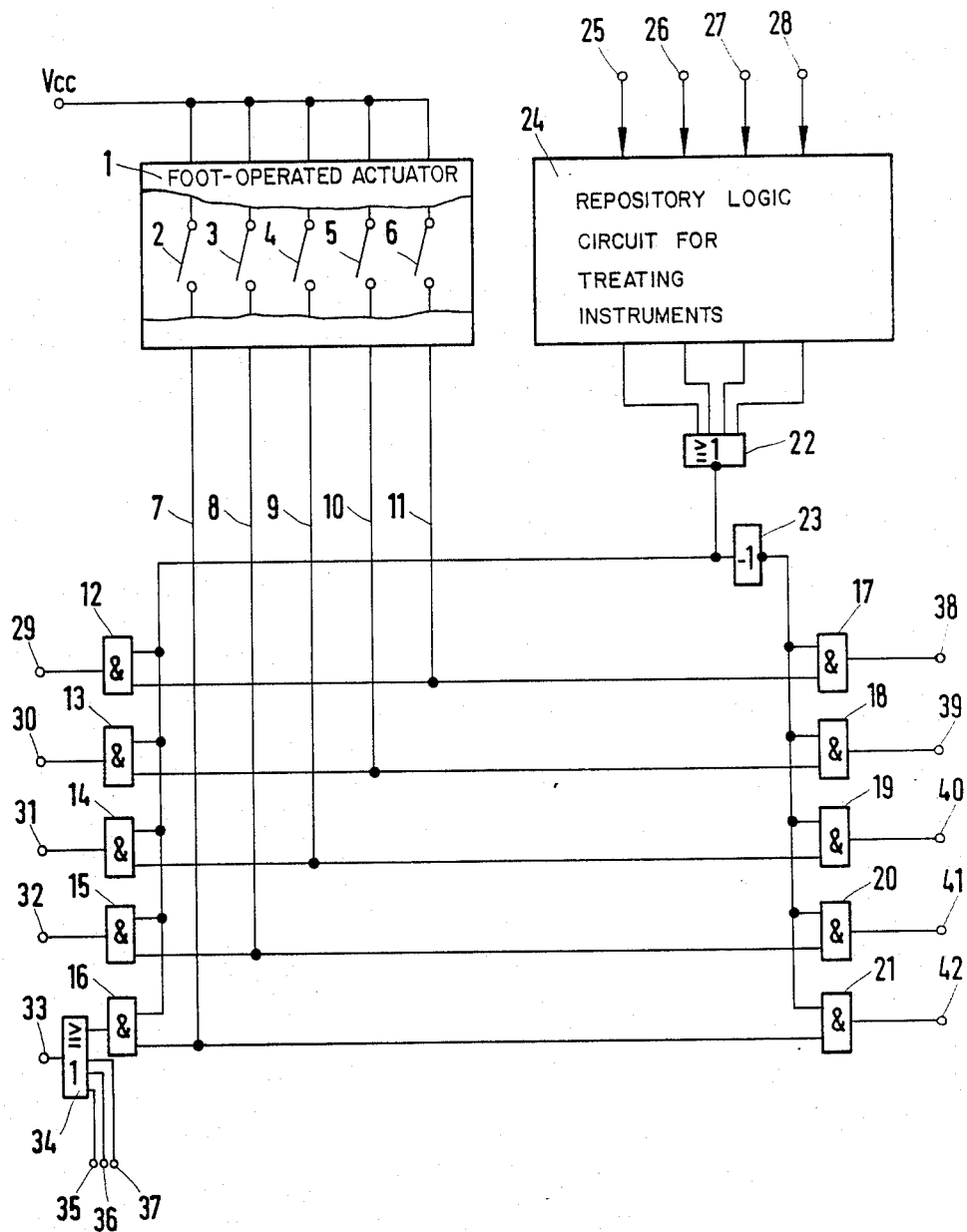

FOOT-OPERATED STARTER FOR A DENTAL TREATMENT LOCATION

BACKGROUND OF THE INVENTION

1. Field of the Invention

The present invention relates to a foot-operated starter or controller for a dental treatment apparatus possessing a patient's or dental chair and a plurality of treating instruments which are arranged in separate repositories, including actuating elements through the actuation of which there can be initiated or varied different functions of the applicable treatment location.

2. Discussion of the Prior Art

Heretofore, every dental treatment apparatus has been equipped with two foot-operated starters. In this instance, one of the foot-operated starters served for the adjustment of the dental chair, whereas the other foot-operated starter served for the control or the actuation of the treating instruments. Furthermore, there is provided the possibility of controlling the collective functions of the treatment location or place through the actuation of hand-operated or manual push-buttons. However, a manual operation of that type is presently not acceptable because of hygienic reasons.

Basically, it is possible to combine the actuating elements of the two foot-operated starters, which have been employed up to the present for each treatment location, into a single foot-operated starter. However, in general, this signifies a need for a relatively high constructive requirement, and moreover, at least the serviceability of that type of complicated foot-operated starter would be rendered more difficult.

SUMMARY OF THE INVENTION

Accordingly, it is an object of the present invention to provide a single foot-operated starter for a dental treatment location or place, which under a relatively low technological requirement, allows for the actuation of, as well as the control over, the dental chair as well as the treating instruments.

The foregoing object is achieved in an inventive mode through the intermediary of a foot-operated starter of the type as mentioned hereinabove, in that the actuating elements are interconnected with a switching or junction circuit arrangement, which is connected in such a manner with display devices indicative of the removal of the treating instruments from their repositories, such that merely upon withdrawal of at least one treating instrument from its repository, the actuating elements serve for the regulation of the adjusted setting of the applicable treating instrument, whereas at the presence of the collective treating instruments in their repositories they serve for the setting of the adjusted positions of the dental chair.

Accordingly, the invention provides the advantage that by means of a single, relatively simply constructable foot-operated starter, it is sufficient to be able to control or adjust the dental chair as well as the treating instruments with respect to their operational parameters.

Preferably, the junction circuit arrangement possesses two groups of AND-elements; whereby one AND-element of the one group of AND-elements and one AND-element of the other group of AND-elements are presently connected in common with respectively one input of one of the actuating elements, whereby the AND-elements of the one group of AND-elements have their other inputs commonly connected to the output of an NOR-element, whose inputs are connected with the above-mentioned display devices, and in which the AND- elements of the other group of AND-elements have their other inputs commonly connected through a negating element at the output of the NOR-element. As a result, there is obtained the advantage of a particularly low requirement on circuitry technology with regard to the actual implementation of the junction circuit arrangement.

Preferably connected with the output of at least one of the AND-elements, whose output signals serve for the control over the adjustment of the dental chair, is an input of an OR-element, to which there can be transmitted further control signals at other inputs. Obtained hereby is the advantage of an additional control capability of the dental chair.

BRIEF DESCRIPTION OF THE DRAWING

Reference may now be had to the following detailed description of an exemplary embodiment of the invention, as represented by a generally schematic block circuit diagram of the inventive treatment location, as illustrated in the accompanying single figure of the drawing.

DETAILED DESCRIPTION

Represented generally schematically in the drawing is a foot-operated starter 1 possessing actuating elements 2, 3, 4, 5 and 6, which are each shown as simple operating contacts. The actuating elements 2 through 6 can be operated either individually or in combination with each other; when they are actuated they connect a supply voltage Vcc to the output conductor of the output conductors 7, 8, 9, 10, 11 which are for the time being connected therewith; this corresponds to the emission of a binary "1" signal.

Connected the presently considered output conductors 7 through 11 is a junction circuit arrangement, which encompasses two groups of junction elements:

Belonging to the one (first) group of junction elements are AND-elements 12, 13, 14, 15, 16, and belonging to the other (second) group of junction elements are AND-elements 17, 18, 19, 20, 21, which are commonly connected with one of their inputs to the output of a negating element 23, and thereby presently fulfill the function of a blocking element.

Presently, one of the AND-elements belonging to the first group of AND-elements 12 through 16, and one of the AND-elements belonging to the second group of AND-elements 17 through 21 are commonly connected with one input thereof to the above-mentioned output condutors 7 through 11. The other inputs of the AND-elements belonging to the first group of AND-elements 12 through 16 are commonly connected to the output of an NOR-element 22, to this output of which there is also connected the input of the mentioned negating element 23. The NOR-element 22 is connected at its input to a repository logic circuit for the treating instruments, which receives signals conducted to the inputs 25, 26, 27, 28, which indicate the presence of the treating instruments in their associated repositories. For example, signals can originate from light barriers.

Connected to the outputs of the AND-elements 12, 13, 14, and 15 belonging to the considered first froup of AND-elements, which are identified by reference numerals 29, 30, 31 and 32, are setting or control devices for the adjustment of the dental chair, which can be actuated by means of the foot-operated starter 1. Connected with the output of the AND-element 16 belonging to the applicable first group of AND-elements, is the one input of an OR-element 34, to which output 33 of the latter of which there can also be connected at setting or control element for the adjustment of the dental chair. The OR-element 34 can have additional control elements for the adjustment of the dental chair conducted thereto at further inputs 35, 36, 37, such as from further operating elements or from an eventually provided additional foot-operated starter.

Connected to the outputs of the AND-elements 17, 18, 19, 20, and 21 identified by reference numerals 38, 39 40, 41, and 42, which belong to the second group of AND-elements are control elements (not shown in the drawing) for the operational setting of the treating instruments. Through the actuation of these control elements it is possible to place into operation, for example, a turbine drill or a normal drilling machine, or there can be emitted by air blow or a spray medium.

Hereinbelow, elucidated in more extensive detail is the mode of operation of the arrangement is illustrated in the drawing.

In this connection, it is assumed that the repository logic 24, when the collective treating instruments are located in their associated repositories, will presently emit a binary signal "0" from their collective outputs. In this instance, the NOR-element 22 emits a binary signal "1" from its output. However, when a treating instrument is removed from its associated repository, then the repository logic 24 will emit a "1" signal from one of its outputs, upon the occurrence of which there is emitted an "0" signal from the output of the NOR-element 22. This "0" signal blocks the transmitting capability of the AND-elements 12 through 16. However, by means of the negating element 23 there is transmitted a "1" signal to one of the inputs of the AND-elements 17 through 21. This has as a result, that through the actuation of the actuating elements 2 through 6 of the foot-operated starter 1, there are now trasmitted, through the AND-elements 17 through 21, binary "1" signals or the voltage Vcc corresponding thereto. Thereby, the foot-operated starter 1 serves for the control over the functions of the treating instruments. In principle, it is thereby possible that, with the assistance of the foot-operated starter 1, there can also be simultaneously controlled the functions of a plurality of treating instruments. For this purpose, there must merely be actuated the applicable actuating elements of the foot-operated starter 1.

When collective treating instruments are again received by their repositories, the repository logic 24 will then presently emit an "0" signal from collective outputs. As a result thereof, the NOR-element 22 will emit a "1" signal from its output, which switches the AND-elements 12 through 16 into the condition capable of transmission. Through the negating element 23 there is now present an "0" signal at the one of the inputs of the collective AND-elements 12 through 17, such that now, with the actuation of the actuating elements 2 through 6 of the foot-operated starter 1, there can be transmitted "1" signals, or the voltage Vcc corresponding thereto, through the AND-elements 12 through 16 to the connections 29 through 33. In this instance, as a result, there are controlled the functions of the dental chair.

As has been already elucidated hereinabove, the output of AND-element 16 is connected through the OR-element 34 with the connection 33. Through this measure in the circuitry there is ensured that certain pre-given functions of the dental chair can then also be set when the foot-operated starter 1 is equipped for merely setting or activating functions of the treating instruments. The control signals which serve for this purpose are conducted to the connections 35, 36, 37; for exampale, at the head of the dental chair.

Finally, it is also to be indicated, that there has been primarily described a junction circuit arrangement which is assembled from digitally-operating linking or junction elements; however, expediently these junction circuit arrangements can also be assembled from other types of components, for example, relays or analog-switches, or with the utilization of so-called bus-operators. Finally, it is also mentioned that the arrangement as illustrated in the drawing can be operated without the utilization of an NOR-element 22, when a binary "0" signal is emitted from the output of the repository logic 24, when at least one of the treating instruments is removed from its associated repository, whereas at the receipt of collective of the treating instruments in their associated repositories, there is emitted a "1" signal.

What is claimed is:

1. A foot-operated starter for adjusting a dental chair and for operating a plurality of treating instruments arranged in separate repositories of a dental treatment apparatus, said starter comprising:

a plurality of actuating elements for actuating different functions of the treatment apparatus, said actuating elements being coupled to a control signal;

display means for indicating the removal of treating instruments from their associated repositories; and a circuit arrangement being coupled to said actuating elements and said display means;

said circuit arrangement comprising first and second groups of AND-elements; a first input of each of the AND-elements of the first group of AND-elements and a first input of each of a corresponding AND-element of the second group of AND-elements being commonly connected with an input of a respective one of the pulrality of actuating elements; the AND-elements of the first group of AND-elements having second inputs commonly connected to the output of an NOR-element, said NOR-element having inputs connected with said display means; and the AND-elements of the second group of AND-elements having second inputs commonly connected through a negating element to the output of the NOR-element;

said circuit arrangement being operable to selectively control the operation of the treating instruments and the adjustment of the dental chair such that upon removal of at least one treating instrument from its repository, the actuating elements provide a control signal to the second group of AND-elements for the setting of the operating parameters of the applicable treating instrument, and upon the presence of all the treating instruments in their repositories, the actuating elements provide a control signal to the first group AND-elements for the setting of the adjustment parameters of the dental chair.

2. A foot-operated starter as claimed in claim 1, wherein the output of at least one of the AND-elements of said first group of AND-elements, the output signals of which serve for the control over the adjustment of the dental chair, is connected to the input of an OR-element, said OR-element having further inputs for receiving control signals.

* * * * *